(12) United States Patent
Sabatake et al.

(10) Patent No.: US 11,325,095 B2
(45) Date of Patent: May 10, 2022

(54) GAS PROCESSING DEVICE

(71) Applicant: Ushio Denki Kabushiki Kaisha, Tokyo (JP)

(72) Inventors: Kenichi Sabatake, Tokyo (JP); Kohei Shigeta, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 17/283,225

(22) PCT Filed: Sep. 11, 2019

(86) PCT No.: PCT/JP2019/035659
§ 371 (c)(1),
(2) Date: Apr. 6, 2021

(87) PCT Pub. No.: WO2020/090238
PCT Pub. Date: May 7, 2020

(65) Prior Publication Data
US 2021/0346861 A1    Nov. 11, 2021

(30) Foreign Application Priority Data

Oct. 30, 2018    (JP) .............................. JP2018-204299

(51) Int. Cl.
*B01J 19/12*    (2006.01)
*A61L 9/015*    (2006.01)
(Continued)

(52) U.S. Cl.
CPC ............. *B01J 19/123* (2013.01); *A61L 9/015* (2013.01); *A61L 9/20* (2013.01); *B01J 19/0013* (2013.01);
(Continued)

(58) Field of Classification Search
CPC .................. B01J 19/123; B01J 19/0013; B01J 2219/0869; B01J 2219/0871;
(Continued)

(56) References Cited

U.S. PATENT DOCUMENTS 5,505,912 A * 4/1996 Hallett ...................... A61L 2/10
422/186.3
6,508,982 B1    1/2003 Shoji
(Continued)

FOREIGN PATENT DOCUMENTS

CN    104023753 A    9/2014
EP    3498666 A1    6/2019
(Continued)

OTHER PUBLICATIONS

Written Opinion issued in PCT/JP2019/035659; dated Dec. 17, 2019.
(Continued)

*Primary Examiner* — Xiuyu Tai
(74) *Attorney, Agent, or Firm* — Studebaker & Brackett PC

(57) ABSTRACT

A gas processing device includes: a casing that includes a first end having a first opening region constituting an intake port, a second end having a second opening region constituting an exhaust port, and a main body portion on the inside of which is formed a hollow portion; a discharge lamp that has a tube body which is disposed in the hollow portion and which has a shape extending in the first direction, a first electrode, and a second electrode, the discharge lamp that emits ultraviolet rays from the tube body; a power supply unit arranged outside the casing; and a first power supply line and a second power supply line that are wired so as to pass through a side closer to the first end than the main body
(Continued)

portion, and that electrically connect the power supply unit to the first electrode and the second electrode.

18 Claims, 4 Drawing Sheets

(51) Int. Cl.
  *A61L 9/20* (2006.01)
  *B01J 19/00* (2006.01)

(52) U.S. Cl.
  CPC .............. *B01J 2219/0869* (2013.01); *B01J 2219/0871* (2013.01); *B01J 2219/0875* (2013.01); *B01J 2219/1203* (2013.01)

(58) Field of Classification Search
  CPC ........ B01J 2219/0875; B01J 2219/1203; B01J 2219/0877; B01J 2219/0892; B01J 35/004; A61L 9/015; A61L 9/20; A61L 2/10; A61L 2/26; A61L 9/046; A61L 9/18; A61L 9/12; A61L 2/202; A61L 2/088; C02F 1/325; C02F 2103/04; C02F 2201/3228; C02F 2101/363; C02F 2201/328; C02F 2201/3223; C02F 2201/324; C02F 1/78; C02F 2305/10; C02F 2303/04; C02F 2201/782; C01B 13/10; A62D 3/176; A62D 2101/22; A62D 2203/10; H01S 3/225; H01L 21/67028; F24F 8/192; F24F 8/22; Y02A 50/20; Y10S 422/906; A01K 63/04
  See application file for complete search history.

(56) References Cited

U.S. PATENT DOCUMENTS

| | | | |
|---|---|---|---|
| 2014/0328720 | A1 | 11/2014 | Mano et al. |
| 2015/0035429 | A1* | 2/2015 | Hishinuma ............. H01J 61/26 313/491 |
| 2017/0326525 | A1* | 11/2017 | Netemeyer .......... B01J 19/2415 |

FOREIGN PATENT DOCUMENTS

| | | |
|---|---|---|
| JP | H11300151 A | 11/1999 |
| JP | 2001-342139 A | 12/2001 |
| JP | 2008027802 A | 2/2008 |
| JP | 2008036168 A | 2/2008 |
| JP | 2008066095 A | 3/2008 |
| JP | 2011101748 A | 5/2011 |
| JP | 2012000216 A | 1/2012 |
| JP | 2020-185532 A | 11/2020 |
| WO | 2018/030144 A1 | 2/2018 |
| WO | 2019131124 A1 | 7/2019 |

OTHER PUBLICATIONS

International Search Report issued in PCT/JP2019/035659; dated Dec. 17, 2019.
An Office Action mailed by China National Intellectual Property Administration dated Jul. 19, 2021, which corresponds to Chinese Patent Application No. 201980062274.4 and is related to U.S. Appl. No. 17/283,225 with English language translation.
The extended European search report issued by the European Patent Office dated Nov. 29, 2021, which corresponds to European Patent Application No. 19880633.3-1012 and is related to U.S. Appl. No. 17/283,225.

* cited by examiner

GAS PROCESSING DEVICE

TECHNICAL FIELD

The present invention relates to a gas processing device, and especially relates to a gas processing device that performs gas processing with ozone generated by irradiating oxygen in a gas with ultraviolet rays.

BACKGROUND ART

A gas containing a predetermined concentration of ozone has sterilizing and deodorizing activities, and is used in various fields. As a method of generating such ozone, a photochemical reaction using an ultraviolet ray source is known.

However, ozone is highly reactive, and it is known that when parts forming a gas processing device are exposed to ozone, oxidation is promoted and deterioration and damage of the parts progress. Therefore, following Patent Document 1 discloses a configuration in which solenoid valves are arranged on an air intake port and an air exhaust port of a tube body in which a discharge lamp is accommodated, and the valves are controlled to be opened and closed according to a concentration of ozone in order to prevent the ozone from leaking out.

PRIOR ART DOCUMENT

Patent Document

Patent Document 1: JP-A-2011-101748

SUMMARY OF THE INVENTION

Problems to be Solved by the Invention

Ozone generated by irradiating oxygen contained in a processing target gas with ultraviolet rays is consumed by reaction with a substance contained in the processing target gas. However, a part of ozone that has not reacted with the substance contained in the processing target gas comes into contact with parts in a gas processing device, and deterioration and damage of the parts progress.

As in Patent Document 1 described above, a configuration that prevents the parts and the like from being exposed to a high concentration of ozone by accommodating the discharge lamp in a dedicated casing, isolating a space in which ozone is generated, and controlling the ozone concentration inside and outside the casing is considered. However, since a power supply line electrically connected to the discharge lamp cannot be separated from the discharge lamp, a part thereof is exposed to the high concentration of ozone, and progress of deterioration and damage thereof is unavoidable.

In view of the above-described problems, an object of the present invention is to provide a gas processing device in which acceleration of deterioration in power supply line is suppressed by a configuration in which the power supply line is not exposed to ozone generated by ultraviolet rays emitted from a discharge lamp.

Means for Solving the Problems

A gas processing device according to the present invention is a gas processing device that irradiates a processing target gas containing oxygen taken in from an air intake port with ultraviolet rays and then discharges the gas from an air exhaust port provided in a position different from a position of the air intake port, and the gas processing device is provided with: a casing including a first end including a first opening region forming the air intake port, a second end arranged in a position separated from the first end in a first direction, the second end including a second opening region forming the air exhaust port, and a main body portion on an inner side of which a hollow portion communicating the first opening region and the second opening region is formed;

a discharge lamp arranged in the hollow portion and including a tube body having a shape extending in the first direction, a first electrode, and a second electrode, the discharge lamp that emits the ultraviolet rays from the tube body by application of a voltage between the first electrode and the second electrode;

a power supply unit arranged outside the casing;

a first power supply line wired so as to pass through a side closer to the first end than the main body portion, the first power supply line that electrically connects the power supply unit to the first electrode; and a second power supply line wired so as to pass through the side closer to the first end than the main body portion, the second power supply line that electrically connects the power supply unit to the second electrode.

The gas processing device of the present invention is connected to an exhaust duct and the like, takes in the processing target gas that flows from the air intake port, and while allowing the processing target gas to flow toward the air exhaust port, allows the processing target gas to come into contact with ozone generated by the ultraviolet rays emitted from the discharge lamp to perform processing.

The ozone is generated when oxygen contained in the processing target gas is irradiated with the ultraviolet rays emitted from the discharge lamp. When the ultraviolet rays are applied to the oxygen contained in the processing target gas, reaction expressed by following equations (1) and (2) progresses and the ozone is generated. In equation (1), $O(^1D)$ represents an oxygen atom in an excited state that exhibits high reactivity. $O(^3P)$ represents an oxygen atom in a ground state. In equation (1), hv represents that the ultraviolet rays are absorbed. $O(^3P)$ generated by equation (1) reacts with oxygen ($O_2$) contained in the processing target gas to generate ozone ($O_3$) according to equation (2).

$$O_2 + h\nu \rightarrow O(^1D) + O(^3P) \qquad (1)$$

$$O(^3P) + O_2 \rightarrow O_3 \qquad (2)$$

The first opening region is an opening region for guiding the processing target gas from outside the gas processing device to the hollow portion. The discharge lamp is accommodated in the hollow portion, and the processing target gas guided to the hollow portion is processed by the ozone generated by irradiation of the ultraviolet rays from the discharge lamp.

The second opening region is an opening region for guiding the gas processed by the gas processing device out of the gas processing device. In the gas processing device of the present invention, an end on which the first opening region is arranged is the first end, and an end on which the second opening region is arranged is the second end.

As described above, the hollow portion is a region where the ozone is brought into contact with the processing target gas taken into the same from the first opening region to process. That is, the processing target gas is taken into the gas processing device from the first opening region, passes through the hollow portion, and is discharged to the outside of the gas processing device from the second opening region. An entire portion including the first opening region, the hollow portion, and the second opening region through which the processing target gas flows is the main body portion.

The discharge lamp is provided with the first electrode and the second electrode to which the voltage is applied. The first electrode and the second electrode are electrically connected to the power supply unit arranged outside the casing via the power supply lines (first power supply line and second power supply line), respectively, and when the voltage is applied from the power supply unit to between the first electrode and the second electrode, the discharge lamp emits the ultraviolet rays.

The gas processing device of the present invention is configured such that both the first power supply line connecting the first electrode of the discharge lamp to the power supply unit and the second power supply line connecting the second electrode to the power supply unit pass through the first end side on which the first opening region for taking in the processing target gas from outside the gas processing device into the gas processing device is arranged.

As described above, the processing target gas flowing through the main body portion is taken into the first opening region, goes to the hollow portion, and is discharged from the second opening region. That is, while the processing target gas is taken into the gas processing device, an air flow is constantly generated in the hollow portion from the first end side to the second end side. Therefore, most of the ozone which is generated in the hollow portion and does not react with the processing target gas goes toward not the first end but the second end to be discharged from the second opening region.

Therefore, by wiring both the first power supply line and the second power supply line so as to pass through the first end side, the first power supply line and the second power supply line are not exposed to the ozone generated in the hollow portion, and progress of deterioration and damage of the first power supply line and the second power supply line is suppressed.

Note that the processing target gas also contains not a little moisture. When the moisture in the processing target gas is irradiated with the ultraviolet rays emitted by the discharge lamp, the reactions expressed by equation (1) above and equation (3) below progress, and hydroxyl radical (—OH) is also generated.

$$O(^1D)+H_2O \rightarrow \cdot OH + \cdot OH \qquad (3)$$

Radical products such as hydroxyl radical are also highly reactive like ozone, and promote deterioration and damage of parts and the like. However, according to the configuration of the present invention, almost all of the radical products generated in the hollow portion go toward not the first end but the second end to be discharged from the second opening region. That is, it is possible to suppress the progress of deterioration and damage of the first power supply line and the second power supply line due to the radical products.

The first opening region may be formed to be narrower toward the second opening region.

When the first opening region is formed to be narrower toward the second opening region, the processing target gas that flows is guided to the hollow portion while being compressed in the first opening region. The processing target gas that travels to the hollow portion while being compressed has a higher pressure in the travel direction and a flow velocity increases. Therefore, the gas in the hollow portion is pushed out to the second end side with a stronger pressure, and the ozone and radical products generated in the hollow portion are less likely to go to the first end, so that a risk of exposure of the first power supply line and the second power supply line to the ozone and radical products is further reduced.

The casing may be provided with a support member that supports the discharge lamp in which a groove in which the first power supply line and the second power supply line may be internally provided is formed on the first end side.

With the above-described configuration, even in a case where a small amount of ozone flows into the first opening region from the hollow portion, the first power supply line and the second power supply line are internally provided in the support member, so that they are protected from direct contact with the ozone.

Furthermore, in the discharge lamp, a high voltage is applied between the first electrode and the second electrode at the time of light emission, and a high voltage difference is generated between the first power supply line and the second power supply line. At that time, depending on a material of coating of each power supply line and the like, there is a possibility that current leakage occurs only when the power supply lines come into contact with each other. Therefore, it is possible to suppress the current leakage by forming the groove in which each power supply line may be independently internally provided in the support member. However, in a case where the current leakage does not occur by contact between the power supply lines, a groove that may accommodate the power supply lines together may be formed.

The discharge lamp may be formed such that the first electrode and the second electrode are opposed to each other across the tube body on an outer wall surface of the tube body, and arranged such that a direction in which the first electrode and the second electrode are opposed to each other and a direction in which the power supply unit is arranged with respect to the discharge lamp are not parallel to each other as seen in the first direction.

With the above-described configuration, it becomes possible to make a twist less likely to occur between the first power supply line and the second power supply line, and make the power supply lines less likely to come into contact with each other in the first opening region.

The discharge lamp may be an excimer lamp filled with a discharge gas containing Xe.

The excimer lamp is characterized in that this is a lamp that emits ultraviolet rays for generating ozone, and that this may obtain a stable output immediately after being turned on, so that this may be restarted without standby time even when this is turned off when it is not needed.

That is, by using the excimer lamp as the discharge lamp, when the processing target gas does not flow, the lamp may be turned off so that the ozone and radical products are not generated. In a case where the standby time is required at the time of restart, the ozone generated during that time might flow to the first end side and come into contact with the first and second power supply lines; however, the excimer lamp does not require the standby time.

According to the above-described configuration, by appropriately controlling the power supply unit, it is possible to stop generation of unnecessary ozone and radical products in a case where the flow of the processing target gas stops, and each power supply line may be protected from exposure to the ozone and radical products.

The gas processing device may be provided with
a power supply box in which the power supply unit is accommodated, in which the power supply box may be arranged such that one flat surface of the power supply box is in contact with a flat surface formed on a side surface of the casing.

The gas processing device is provided with the power supply box in which the power supply unit may be accommodated, and the power supply box is arranged such that one flat surface of the power supply box is in contact with the flat surface formed on the side surface of the casing, so that the gas processing device in which the casing and the power supply box are integrated may be formed. For example, by forming such that shapes of the contact surfaces of the power supply box and the casing are the same such that they have a rectangular parallelepiped shape as a whole, it becomes easy to stack or align in a case where a plurality of same gas processing devices are arranged so as to conform to the number of ducts, and a flexible arrangement configuration may be taken.

The power supply box may be provided with a cooling air intake port, a cooling air exhaust port, and a cooling fan, and it may be configured that outside air different from the processing target gas, taken into the power supply box from the cooling air intake port by operation of the cooling fan is discharged from the cooling air exhaust port after cooling the power supply unit.

With the above-described configuration, the power supply unit may be cooled by the outside air instead of the processing target gas. By cooling the power supply unit by the outside air, a clean state of a part of the power supply unit and the power supply line arranged in the power supply box may be maintained as compared with a case where this is continuously exposed to the processing target gas and the processed gas, and progress of deterioration and damage is suppressed.

Effect of the Invention

According to the present invention, a gas processing device is realized in which a power supply line is not exposed to ozone generated by ultraviolet rays emitted from a discharge lamp and acceleration of deterioration of the power supply line is suppressed.

MODE FOR CARRYING OUT THE INVENTION

Figure 1:
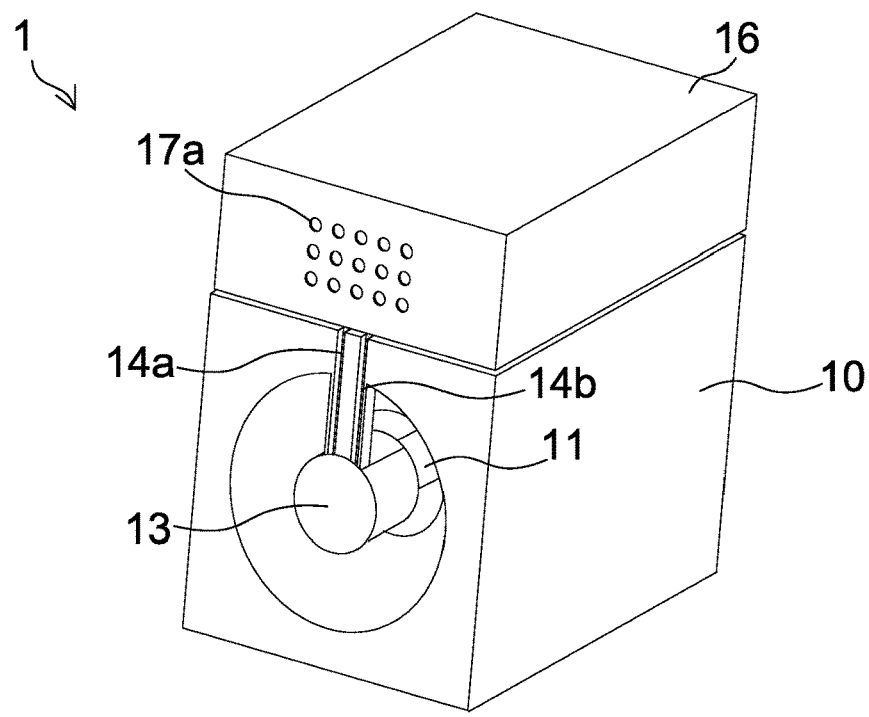
FIG. 1 is a schematic entire perspective view of an embodiment of a gas processing device.

A gas processing device of the present invention is hereinafter described with reference to the drawings. Note that each of the following drawings is schematic illustration, and a dimensional ratio and the number in the drawings do not necessarily coincide with actual dimensional ratio and number.

FIG. 1 is a schematic entire perspective view of an embodiment of a gas processing device. A gas processing device 1 in this embodiment is obtained by stacking a casing 10 through which a processing target gas flows and a power supply box 16 in which a power supply unit 15 is accommodated and has a rectangular parallelepiped shape as a whole. Structures of the casing 10 and the power supply box 16 are described later in detail.

Figure 2:
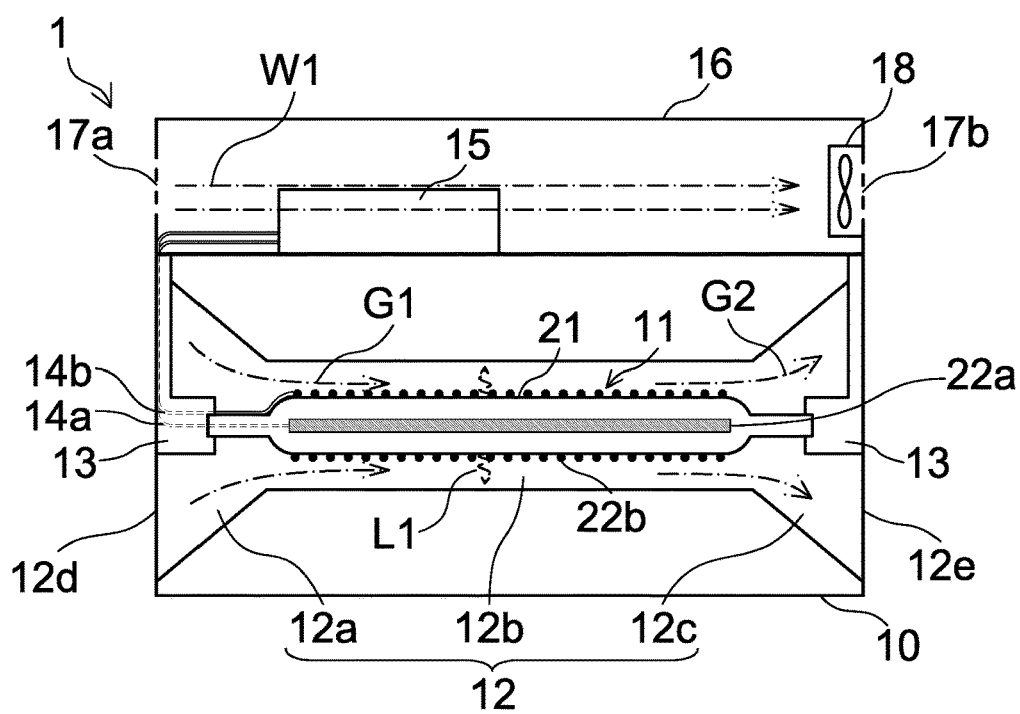
FIG. 2 is a schematic cross-sectional view of the gas processing device illustrated in FIG. 1 as seen from the side.

FIG. 2 is a schematic cross-sectional view of the gas processing device 1 illustrated in FIG. 1 as seen from the side. As illustrated in FIG. 2, the casing 10 is provided with a main body portion 12 including a hollow portion 12b, and a first end 12d and a second end 12e located on both ends of the main body portion 12. The first end 12d is provided with a first opening region 12a communicated with the hollow portion 12b. The second end 12e is provided with a second opening region 12c communicated with the hollow portion 12b in a position on a side opposite to the first opening region 12a. A discharge lamp 11 is arranged inside the hollow portion 12b along a tube axis of the main body portion 12.

As illustrated in FIG. 2, the power supply unit 15 is arranged in the power supply box 16. The discharge lamp 11 to which a voltage is applied from the power supply unit 15 emits ultraviolet rays L1. When a processing target gas G1 is taken in from outside the gas processing device 1 through the first opening region 12a, this is guided to the hollow portion 12b. The processing target gas G1 that flows through the hollow portion 12b reacts with ozone and radical products generated by irradiation of the ultraviolet rays L1 from the discharge lamp 11, and a substance contained in the processing target gas G1 (processing target substance) is processed. A processed gas G2 obtained after processing in this manner is discharged out of the gas processing device 1 from the second opening region 12c side. A structure of the discharge lamp 11 is described later.

Furthermore, the gas processing device 1 illustrated in FIG. 2 is provided with support members 13 for supporting the discharge lamp 11 arranged in the hollow portion 12b in positions of the first end 12d and the second end 12e.

Both the first opening region 12a and the second opening region 12c are formed to be narrower toward the hollow portion 12b. Because the first opening region 12a becomes narrower toward the second opening region 12c, a pressure in a travel direction of the processing target gas G1 flowing through the hollow portion 12b increases, and a flow velocity of the processing target gas G1 increases. Therefore, an effect of pushing the ozone generated by the ultraviolet rays L1 emitted from the discharge lamp 11 toward the second opening region 12c is enhanced.

A case is assumed where the gas processing device 1 is directly connected to an air conditioning duct of a building or an exhaust processing duct of a factory, for example, to be used. In this case, opening diameters of the first opening region 12a and the second opening region 12c on the first end 12d and the second end 12e, respectively, are preferably made the same as a diameter of the air conditioning duct, and in most cases, the opening diameter is made about 15 cm.

The hollow portion 12b is configured such that a gap between an outer wall surface of a tube body 21 forming the discharge lamp 11 and an inner wall surface in a site of the hollow portion 12b of the casing 10 is as narrow as possible such that the processing target gas G1 is brought into contact with the ozone. The gap is preferably about 1 cm. Specifically, the discharge lamp 11 arranged in the hollow portion 12b is formed with a diameter or a width of the tube body 21 of about 3 cm to 5 cm, and an opening diameter of the hollow portion 12b of the casing 10 is made about 4 cm to 6 cm.

In this embodiment, as described above, the power supply unit 15 is accommodated in the dedicated power supply box 16. The power supply box 16 is arranged so as to come into contact with a flat surface forming an outer wall surface of the casing 10. Furthermore, the power supply box 16 is provided with a cooling air intake port 17a for taking in cooling air W1 for cooling the power supply unit 15, a cooling air exhaust port 17b for discharging the cooling air W1, and a cooling fan 18 for blowing the cooling air W1. In this embodiment, the cooling fan 18 is arranged at the cooling air exhaust port 17b, but this may also be arranged at the cooling air intake port 17a.

Since the power supply unit 15 accommodated in the power supply box 16 is cooled by outside air taken in through the cooling air intake port 17a, the power supply unit 15 may maintain a cleaner state for a long period of time than a case where this is cooled by the processing target gas G1 or the processed gas G2.

The discharge lamp 11 and the power supply unit 15 are electrically connected to each other with a first power supply line 14a and a second power supply line 14b. When a voltage is applied from the power supply unit 15 to between the first power supply line 14a and the second power supply line 14b, the ultraviolet rays L1 are emitted from the discharge lamp 11.

Figure 3:
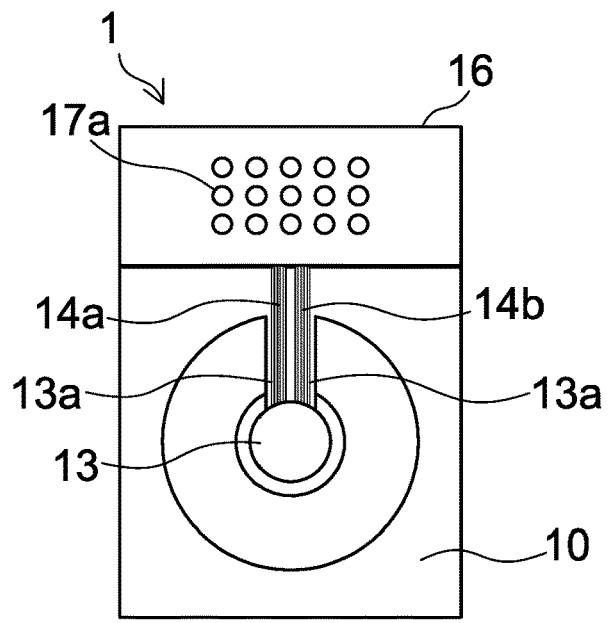
FIG. 3 is a front view of the gas processing device in FIG. 1 as seen from a first end side in a travel direction of a processing target gas.

Both the first power supply line 14a and the second power supply line 14b are wired so as to pass through the first end 12d side. This is described with reference also to FIG. 3. FIG. 3 is a front view of the gas processing device 1 in FIG. 1 as seen from the first end 12d side in a tube axis direction of the discharge lamp 11. As illustrated in FIG. 3, two grooves 13a are formed in the support member 13, and the power supply lines (14a and 14b) are independently internally provided therein. As a result, even in a case where the ozone and radical products generated in the hollow portion 12b flow into the first opening region 12a, they may be less likely to come into contact with the power supply lines (14a and 14b).

By independently internally providing the power supply lines (14a and 14b) in the grooves 13a, both the lines may be separated by a certain distance or more. As a result, an effect of suppressing a leakage current generated between the power supply lines (14a and 14b) may also be obtained even in a case where a high voltage is applied when the discharge lamp 11 is lit. When the high voltage is applied to the power supply lines (14a and 14b), there is a case where the leakage current is generated only when both the lines come into contact with each other, although it depends on a material and a thickness of a coating of each of the power supply lines (14a and 14b). Therefore, it is preferable to wire both the power supply lines (14a and 14b) so as to be separated from each other, and a separation distance may be secured by wiring them by using the grooves 13a as described above.

Note that, in a configuration in which the power supply lines (14a and 14b) are internally provided in the support member 13, in addition to the grooves 13a, a cavity may be formed inside the support member 13, and the power supply lines (14a and 14b) may be wired therein.

As illustrated in FIG. 2, the discharge lamp 11 is formed of a cylindrical first electrode 22a extending along the tube axis in the cylindrical tube body 21 and a second electrode 22b that covers the outer wall surface of the tube body 21 in a mesh pattern, and the tube body 21 is filled with a discharging gas containing Xe. Here, the first electrode 22a and the second electrode 22b are electrically connected to the first power supply line 14a and the second power supply line 14b, respectively, on the first end 12d side.

The discharge lamp 11 may also be the discharge lamp 11 having a so-called double tube structure. The discharge lamp 11 having the double tube structure is the discharge lamp 11 having a double cylindrical structure in which one electrode 22a is arranged on an inner wall surface of an inner tube, and the other electrode 22b is arranged on an outer wall surface of an outer tube.

Figure 4A:
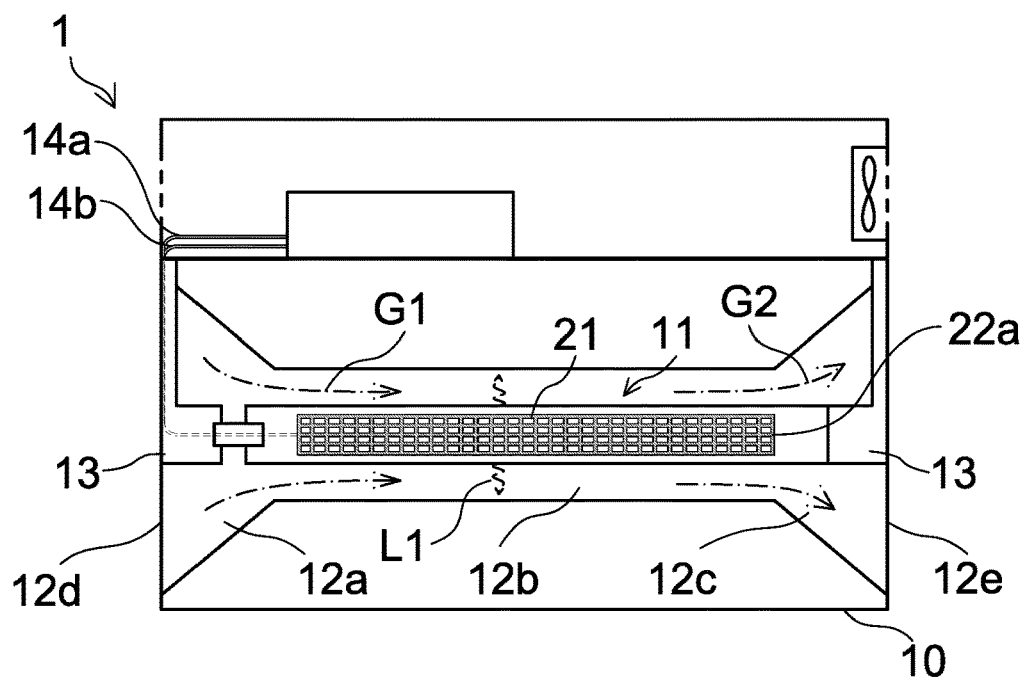
FIG. 4A is a schematic cross-sectional view of the gas processing device by a discharge lamp having a flat tube structure as seen from the side.
Figure 4B:
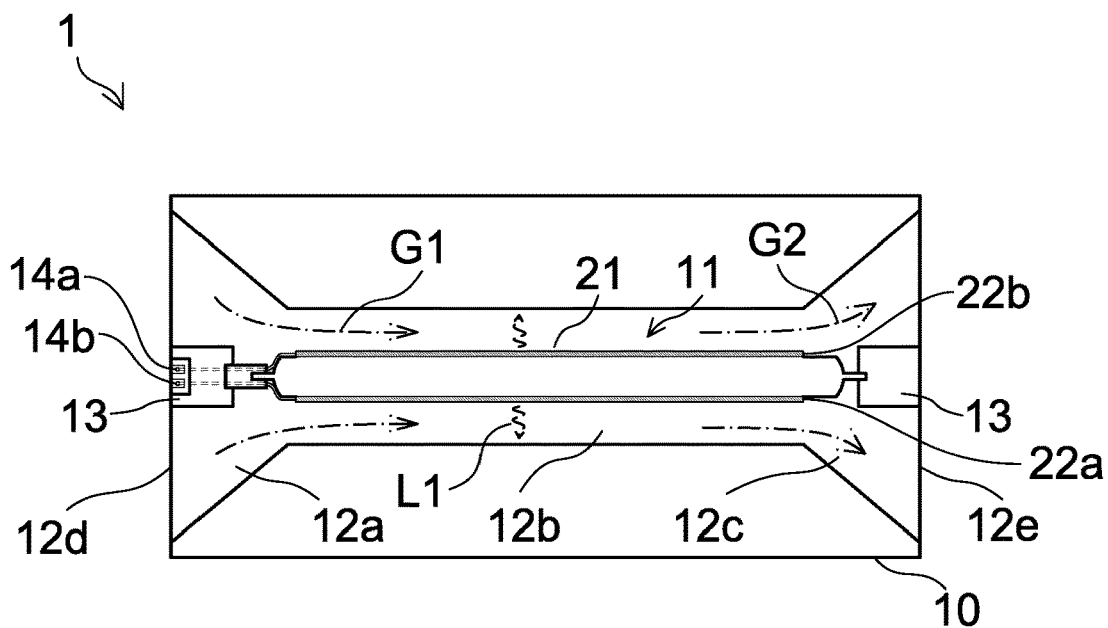
FIG. 4B is a schematic cross-sectional view of the gas processing device by the discharge lamp having the flat tube structure as seen from above.

Furthermore, the discharge lamp 11 may be the discharge lamp 11 having a so-called flat tube structure. The discharge lamp 11 having the flat tube structure is described with reference to FIGS. 4A, 4B, and 4C. FIG. 4A is a schematic cross-sectional view of the gas processing device 1 by the discharge lamp 11 having the flat tube structure as seen from the side. FIG. 4B is a schematic cross-sectional view of the gas processing device 1 by the discharge lamp 11 having the flat tube structure as seen from above. As illustrated in FIG. 4A, the discharge lamp 11 having the flat tube structure is the discharge lamp 11 including the tube body 21 having a rectangular tube shape in which the electrode 22a is provided on one outer wall of a pair of outer walls facing each other of the tube body 21 and the electrode 22b is provided on the other outer wall, so that both the electrodes (22a and 22b) are provided so as to be separated from each other. As illustrated in FIG. 4B, both the electrodes (22a and 22b) of the discharge lamp 11 having the flat tube structure are formed into a mesh shape.

Figure 4C:
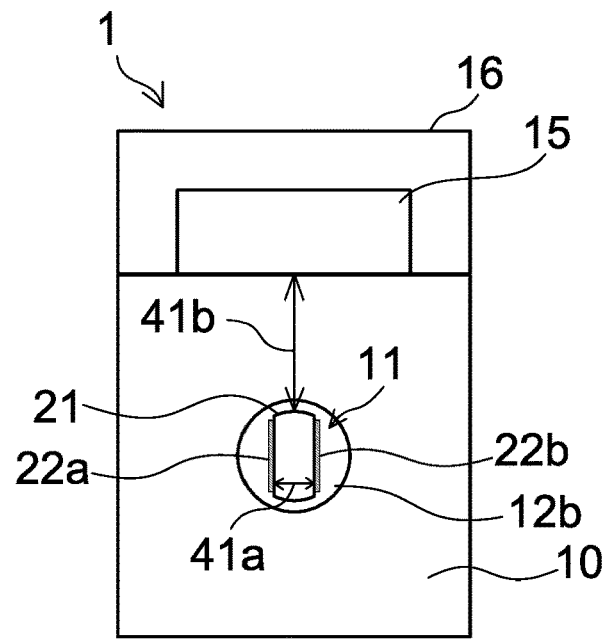
FIG. 4C is a schematic cross-sectional view of the gas processing device by the discharge lamp having the flat tube structure as seen front the front.

FIG. 4C is a schematic cross-sectional view of the gas processing device 1 by the discharge lamp 11 having the flat tube structure as seen from the front. As illustrated in FIG. 4C, the discharge lamp 11 having the flat tube structure is arranged such that an opposing direction 41a of the first electrode 22a and the second electrode 22b is orthogonal to an arranging direction 41b of the power supply unit 15 with respect to the discharge lamp 11 as seen in the tube axis direction of the tube body 21. By arranging the discharge lamp 11 in this manner, as illustrated in FIG. 4B, the power supply lines (14a and 14b) are wired so as to be separated from each other, a twist of the first power supply line 14a and the second power supply line 14b is less likely to occur, the power supply lines (14a and 14b) hardly come into contact with each other, and current leakage between the power supply lines (14a and 14b) may be suppressed.

In a case where the discharge lamp 11 is an excimer lamp filled with the discharging gas containing Xe, the structure illustrated in FIGS. 2 to 4C is merely an example and a shape is not limited to this. In order for the ozone to be generated by the ultraviolet rays L1 emitted by the discharge lamp 11, the ultraviolet rays L1 preferably have a short wavelength, and specifically, the lamp preferably may emit the ultraviolet rays L1 having a wavelength of 200 nm or shorter.

The discharge lamp 11 and the power supply unit 15 are connected to each other by the power supply lines (14a and 14b). Inside the discharge lamp 11, the power supply line 14a is electrically connected to the electrode 22a on the first opening region 12a side, and outside the discharge lamp 11, the power supply line 14b is electrically connected to the electrode 22b on the first opening region 12a side. When the voltage output from the power supply unit 15 is applied to the electrodes (22a and 22b) through the power supply lines (14a and 14b), respectively, the discharge lamp 11 emits light, and the ultraviolet rays L1 are emitted to the processing target gas G1.

Coating materials of the power supply lines (14a and 14b) include polyvinyl chloride, polyethylene, and Teflon®. Polyvinyl chloride and polyethylene have very low resistance to ozone and radical products, and when exposed to a high concentration of ozone and radical products, they deteriorate in a short period of time. Teflon® has higher resistance than polyvinyl chloride and polyethylene, but deterioration progresses slightly.

In the vicinity of the discharge lamp 11, the ozone and radical products are constantly generated while the processing target gas G1 flows and the discharge lamp 11 emits the ultraviolet rays L1. Then, the ozone and radical products generated in the hollow portion 12b are swept downstream toward the second opening region 12c by the processing target gas G1 flowing from the upstream.

The first power supply line 14a and the second power supply line 14b are wired on the first opening region 12a side located upstream of the hollow portion 12b and are not exposed to the ozone and radical products generated in the hollow portion 12b, so that the progress of deterioration and damage by the ozone and radical products is suppressed.

Another Embodiment

Hereinafter, another embodiment of a gas processing device 1 is described.

Figure 5:
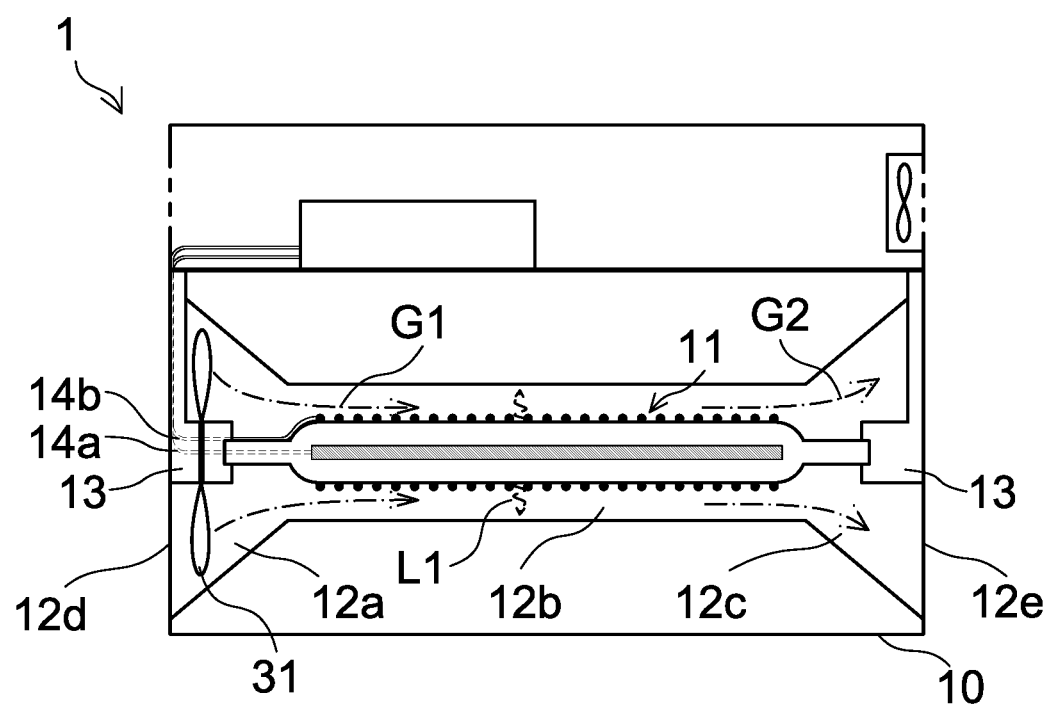
FIG. 5 is a schematic cross-sectional view of another embodiment of a gas processing device as seen from the side.

<1> FIG. 5 is a schematic cross-sectional view of the gas processing device 1 as seen from the side. As illustrated in FIG. 5, a blower fan 31 may be provided on a first opening region 12a or a second opening region 12c so that a processing target gas G1 and a processed gas G2 in a main body portion 12 and ozone and radical products generated in a hollow portion 12b constantly flow toward a second opening region 12c.

Note that, when the blower fan 31 is arranged in the second opening region 12c, this is exposed to the ozone and radical products generated in the hollow portion 12b. Therefore, from the viewpoint of preventing the blower fan 31 from deteriorating, it is preferable to provide the blower fan 31 in the first opening region 12a.

<2> A valve may be provided between the first opening region 12a and the hollow portion 12b so that the ozone and radical products generated in the hollow portion 12b do not flow to the first opening region 12a.

<3> The configuration of the gas processing device 1 described above is merely an example, and the present invention is not limited to each of the illustrated configurations.

For example, the main body portion 12 may have the same opening diameter from the first end 12d to the second end 12e. It does not matter if the power supply lines (14a and 14b) may not be internally provided in the grooves 13a formed in the support member 13.

Although a case where one surface of the power supply box 16 is arranged so as to be in contact with the surface of the casing 10 is illustrated in FIGS. 1 and 2, they may also be arranged in separate positions. Furthermore, although a case where the power supply unit 15 is arranged in a space enclosed by the power supply box 16 is illustrated in FIGS. 1 and 2, it does not matter if the power supply unit 15 is exposed in a position outside the casing 10. In this case, the cooling air intake port 17a, the cooling air exhaust port 17b, and the cooling fan 18 may not be necessarily required.

<4> In the above-described embodiment, as illustrated in FIG. 4C, the discharge lamp 11 having the flat tube structure is arranged such that the opposing direction 41a of the first electrode 22a and the second electrode 22b is orthogonal to the arranging direction 41b of the power supply unit 15 with respect to the discharge lamp 11 as seen in the tube axis direction of the tube body 21. However, it is sufficient that an angle formed by the opposing direction 41a and the arranging direction 41b is at least not parallel to each other, and this is preferably 60° or larger and 120° or smaller, and more preferably 70° or larger and 110° or smaller. By designing such that the angle formed by the opposing direction 41a and the arranging direction 41b is within this angle range, it becomes easy to wire the power supply lines (14a and 14b) so as not to be easily twisted with the separation distance (insulation distance) kept, and the current leakage between the power supply lines (14a and 14b) may be suppressed. From the viewpoint of device design, it is desirable to arrange the power supply unit 15 in this manner.

DESCRIPTION OF REFERENCE SIGNS

1 Gas processing device
10 Casing
11 Discharge lamp
12 Main body portion
12a First opening region
12b Hollow portion
12c Second opening region
12d First end
12e Second end
13 Support member
14a First power supply line
14b Second power supply line
15 Power supply unit
16 Power supply box
17a Cooling air intake port
17b Cooling air exhaust port
18 Cooling fan
21 Tube body
22a First electrode
22b Second electrode
31 Blower fan
41a Opposing direction
41b Arranging direction
G1 Processing target gas
G2 Processed gas
L1 Ultraviolet rays
W1 Cooling air

The invention claimed is:

1. A gas processing device that irradiates a processing target gas containing oxygen taken in from an air intake port with ultraviolet rays and then discharges the gas from an air exhaust port provided in a position different from a position of the air intake port, the gas processing device comprising:

a casing including a first end including a first opening region forming the air intake port, a second end arranged in a position separated from the first end in a first direction, the second end including a second opening region forming the air exhaust port, and a main body portion having a hollow portion therein, the hollow portion communicating with the first opening region and the second opening region;

a discharge lamp arranged in the hollow portion and including a tube body having a shape extending in the first direction, a first electrode, and a second electrode, the discharge lamp that emits the ultraviolet rays from the tube body by application of a voltage between the first electrode and the second electrode;

a power supply unit arranged outside the casing;

a first power supply line wired so as to pass through a side closer to the first end than the main body portion, the first power supply line that electrically connects the power supply unit to the first electrode; and a second power supply line wired so as to pass through the side closer to the first end than the main body portion, the second power supply line that electrically connects the power supply unit to the second electrode, wherein the first power supply line and the second power supply line are each wired so as to pass through the first opening region side in the main body portion.

2. The gas processing device according to claim 1, wherein
the first opening region is formed so as to be narrower toward the second opening region.

3. The gas processing device according to claim 1, wherein
the casing is provided with a support member that supports the discharge lamp in which a groove in which the first power supply line and the second power supply line are internally provided is formed on a side of the first end.

4. The gas processing device according to claim 1, wherein
the discharge lamp is formed such that the first electrode and the second electrode are opposed to each other across the tube body on an outer wall surface of the tube body, and arranged such that a direction in which the first electrode and the second electrode are opposed to each other and a direction in which the power supply unit is arranged with respect to the discharge lamp are not parallel to each other as seen in the first direction.

5. The gas processing device according to claim 1, wherein
the discharge lamp is an excimer lamp filled with a discharge gas containing Xe.

6. The gas processing device according to claim 1, further comprising:
a power supply box in which the power supply unit is accommodated, wherein
the power supply box is arranged such that one flat surface of the power supply box is in contact with a flat surface formed on a side surface of the casing.

7. The gas processing device according to claim 6, wherein
the power supply box is provided with a cooling air intake port, a cooling air exhaust port, and a cooling fan, and
the gas processing device is configured such that outside air different from the processing target gas, taken into the power supply box from the cooling air intake port by operation of the cooling fan is discharged from the cooling air exhaust port after cooling the power supply unit.

8. The gas processing device according to claim 2, wherein
the casing is provided with a support member that supports the discharge lamp in which a groove in which the first power supply line and the second power supply line are internally provided is formed on a side of the first end.

9. The gas processing device according to claim 2, wherein
the discharge lamp is formed such that the first electrode and the second electrode are opposed to each other across the tube body on an outer wall surface of the tube body, and arranged such that a direction in which the first electrode and the second electrode are opposed to each other and a direction in which the power supply unit is arranged with respect to the discharge lamp are not parallel to each other as seen in the first direction.

10. The gas processing device according to claim 3, wherein
the discharge lamp is formed such that the first electrode and the second electrode are opposed to each other across the tube body on an outer wall surface of the tube body, and arranged such that a direction in which the first electrode and the second electrode are opposed to each other and a direction in which the power supply unit is arranged with respect to the discharge lamp are not parallel to each other as seen in the first direction.

11. The gas processing device according to claim 8, wherein
the discharge lamp is formed such that the first electrode and the second electrode are opposed to each other across the tube body on an outer wall surface of the tube body, and arranged such that a direction in which the first electrode and the second electrode are opposed to each other and a direction in which the power supply unit is arranged with respect to the discharge lamp are not parallel to each other as seen in the first direction.

12. The gas processing device according to claim 2, wherein
the discharge lamp is an excimer lamp filled with a discharge gas containing Xe.

13. The gas processing device according to claim 3, wherein
the discharge lamp is an excimer lamp filled with a discharge gas containing Xe.

14. The gas processing device according to claim 4, wherein
the discharge lamp is an excimer lamp filled with a discharge gas containing Xe.

15. The gas processing device according to claim 8, wherein
the discharge lamp is an excimer lamp filled with a discharge gas containing Xe.

16. The gas processing device according to claim 9, wherein
the discharge lamp is an excimer lamp filled with a discharge gas containing Xe.

17. The gas processing device according to claim 10, wherein
the discharge lamp is an excimer lamp filled with a discharge gas containing Xe.

18. The gas processing device according to claim 11, wherein
the discharge lamp is an excimer lamp filled with a discharge gas containing Xe.

* * * * *